(12) United States Patent
Faccioli et al.

(10) Patent No.: US 7,270,667 B2
(45) Date of Patent: Sep. 18, 2007

(54) DEVICE FOR THE MANUAL METERING OF A MEDICAL FLUID, PARTICULARLY BONE CEMENT

(75) Inventors: Giovanni Faccioli, Monzambano (IT); Renzo Soffiatti, Nogara (IT)

(73) Assignee: TECRES SpA, Sommacampagna (IT)

( * ) Notice: Subject to any disclaimer, the term of this patent is extended or adjusted under 35 U.S.C. 154(b) by 167 days.

(21) Appl. No.: 10/494,574

(22) PCT Filed: Jun. 18, 2003

(86) PCT No.: PCT/IB03/02349

§ 371 (c)(1),
(2), (4) Date: May 6, 2004

(87) PCT Pub. No.: WO2004/002375

PCT Pub. Date: Jan. 8, 2004

(65) Prior Publication Data
US 2004/0260304 A1 Dec. 23, 2004

(30) Foreign Application Priority Data
Jun. 26, 2002 (IT) .............................. VI2002A0140

(51) Int. Cl.
*A61B 17/58* (2006.01)
(52) U.S. Cl. ......................................................... 606/94
(58) Field of Classification Search ............ 606/92–94; 222/326, 390; 433/89, 90
See application file for complete search history.

(56) References Cited

U.S. PATENT DOCUMENTS 3,417,971 A 12/1968 Blank et al.
4,485,944 A * 12/1984 Eichholz ...................... 222/390
4,583,974 A * 4/1986 Kokernak .................... 604/211
4,832,692 A * 5/1989 Box et al. ................. 604/99.01
5,306,248 A * 4/1994 Barrington ............... 604/97.02
6,676,663 B2 * 1/2004 Higueras et al. .............. 606/93
2004/0204715 A1 * 10/2004 Evans et al. ................... 606/92

FOREIGN PATENT DOCUMENTS

| WO | 99 49819 | 10/1999 |
| WO | 99 65597 | 12/1999 |
| WO | 01 93787 | 12/2001 |

\* cited by examiner

Primary Examiner—Eduardo C. Robert
Assistant Examiner—Richard R Shaffer
(74) Attorney, Agent, or Firm—Dykema Gossett PLLC (57) ABSTRACT

A device for the manual metering of a medical fluid, such as a hardening resin of the bone cement type, comprises a chamber for the fluid to be metered (2, 102) with an end opening (6), a gripping handle (7, 107), a piston (10, 110) which is housed in the chamber (2, 102) and provided with an operating member (12) for a user, and screw-type actuating means (13) arranged in between the operating member (12) and the piston (10) so as to perform the longitudinal movement thereof and pressurise the fluid to be metered. The screw means (13) may be modified so as to change from an operative configuration, where the piston is fed micrometrically, to an inoperative configuration, where the piston may move freely. The screw means (13) comprise an outer thread (14, 114) associated with the piston (10) and a female-thread element (15, 115) formed integrally on the handle (7, 107); the handle may be deformed elastically by means of transverse compression so as to change the screw means (13) from their operative configuration to their inoperative configuration.

10 Claims, 5 Drawing Sheets

DEVICE FOR THE MANUAL METERING OF A MEDICAL FLUID, PARTICULARLY BONE CEMENT

TECHNICAL FIELD

The present invention relates to a device for the manual metering of a fluid for medical applications, such as a medical product in a liquid or paste state, a bone cement, a gypsum or a similar material.

The device according to the invention preferably has a practical application in vertebral plastic surgery and in other medical treatments and in general in all sectors of medicine in which it is necessary to deliver and meter in a controlled manner a product which is in a plastic or viscous state and is prepared, as required, for medications, operations or surgery.

BACKGROUND ART

Metering devices of the type indicated above are known and generally comprise a substantially cylindrical metering chamber with an outlet opening for the fluid or resin to be metered, a gripping handle which can be fixed to the metering chamber, and a rod with a piston housed in the metering chamber in order to expel the fluid through the outlet opening. The piston is located at a longitudinal end of a rod which has at its opposite end an operating member which may be actuated manually by a user.

In order to allow accurate metering under pressure, especially where the fluid is in paste form or has a high viscosity, screw-type actuating means are envisaged and essentially consist of a thread which is formed on the outer surface of the rod with the piston and is intended to co-operate a female thread associated with the metering chamber. By imparting a rotation to the threaded rod by means of the operating member, the piston is made to move along the metering chamber causing the resin to be expelled in a controlled manner.

An example of a metering device of the type mentioned above is illustrated in German application DE-A-3,443,167. A drawback of said known device consists in the fact that, in order to fill the metering chamber in situ with the resin or bone cement to be metered, it is necessary to rotate the threaded rod in the opposite direction to that of delivery, which requires a certain time during which the resin may harden at least partially, reducing its fluidity and plasticity.

In order to prevent this problem, a number of manual metering devices of the type illustrated in European patent application EP-A-1,054,231 and French application FR-A-2,690,332 have been proposed, in which the metering chamber is provided with a lateral opening—which is different from the outlet opening—for the introduction of the fluid to be metered into the chamber.

The opening for introducing the resin is connected by means of a connecting line to a storage tank or an auxiliary syringe for introducing the fluid, which must necessarily be loaded beforehand in one of said auxiliary containers.

A drawback of said known former solution consists in its relative complexity and dimensions. Moreover, the procedure of transferring the fluid into the chamber is fairly long and elaborate and may lead to the partial hardening of said resin.

Dispensers of plastic fluids, such as gypsum or mastics, are known from U.S. Pat. No. 4,485,944 and U.S. Pat. No. 5,253,589, in which it is possible to change over from actuation of the piston with screw means to direct longitudinal actuation without screw means.

Another device of this type, which has the specific function of performing vertebral plastic surgery operations, is described in European patent application EP-A-1,157,677 and comprises a piston which may be actuated either with a screw mechanism or by means of a simple longitudinal movement without a screw mechanism. In particular, the female thread is formed by teeth which engage with the threaded rod in such a way as to transform the rotary movement of the threaded rod into the translatory movement of the piston. However, by moving the teeth away from the threaded rod, this rod may be freely moved axially so as to exert direct pressure on the bone cement. For this purpose, the teeth may slide inside the gripping handle against the opposing action of a spring and may be moved away from and towards the threaded rod by operating a lateral slider which protrudes from the handle.

Owing to this configuration, after operating the slider in order to move the teeth away from the threaded rod, the bone cement may be pressurised inside the metering chamber, both during intake and during delivery, as occurs with a normal syringe. At this point, after bringing the teeth towards the threaded rod by operating the slider, it is possible to perform micrometric feeding of the piston by rotating the operating member.

The main drawback of this known device consists in the significant constructional complexity of the mechanism for actuating the teeth, as well as the large number of component parts, resulting in the consequent high cost of the device as a whole.

This significant cost makes it disadvantageous from a cost-related point of view to use the device once only and therefore results in the need for the device to be cleaned and sterilised in an autoclave or applying other methods every time it is used, with the resultant need to use materials which are of high quality and/or resistant to heat and sterilisation procedures.

Another and perhaps greater drawback consists in the fact that the lateral slider must be moved with one finger of the hand while the other fingers grasp the handle and this makes the operation of disengaging the teeth difficult, especially where fluids and moisture are present in the operating area.

It is therefore possible that the doctor or surgeon, whose hands are normally covered in blood and other body fluids, will be unable to operate the slider easily and will be forced to ask for help or to use the other hand, in circumstances where it is necessary to act rapidly, also because the cement hardens in just a few minutes.

Last but not least another drawback consists in the fact that said known device has a slider on just one side, in particular on the left side, so as to allow the threaded rod to be actuated with the right hand, and therefore cannot be easily used by left-handed people.

It would be convenient to have a metering device which is more functional and can be handled easily compared to known metering devices in all conditions of use and by any user.

Moreover, it would be desirable to have a metering device which has a greater constructional simplicity so as to reduce its production cost considerably. In this way, after its initial use in conditions of maximum hygiene and safety, the metering device could be thrown away, avoiding laborious and costly cleaning and sterilisation operations.

DISCLOSURE OF THE INVENTION

A main object of the present invention is that of designing an improved metering device which allows a fluid at high pressure to be metered micrometrically and to be used like a traditional syringe and which has characteristics of high effectiveness and ease of handling with just one hand.

A further object is that of providing a metering device having an extremely simple structure and low cost structure so that it may be thrown away after every single use.

Last but not least another object is that of providing a metering device which may be made of materials which are not expensive and with components which may be obtained easily on the market so as to make disposable use thereof convenient.

These objects, as well as others which will emerge more clearly hereinafter, are achieved by a device for the manual delivery of a medical fluid, such as a hardening resin of the bone cement type, which comprises, according to claim 1, a metering chamber for the fluid with an end opening, a gripping handle, a piston which is housed in said chamber and provided with an operating member for a user, and screw-type actuating means arranged in between said operating member and said piston so as to perform the longitudinal movement thereof and pressurise the fluid to be metered, it being possible to modify said screw means so as to change from an operative configuration, where the piston is fed micrometrically, to an inoperative configuration, where the piston may move freely, characterized in that said screw Wyleans comprise an outer thread associated with said piston and a female-thread element formed integrally on said handle, said handle being elastically deformable by means of transverse compression so as to change said screw means from said operative configuration said inoperative configuration.

Owing to this configuration, the device according to the invention will have an extremely simplified structure which allows it to be changed from a configuration for micrometric feeding to that of a simple manual syringe, with an extremely simplified structure and an extremely low production cost so as to avoid its repeated use.

BRIEF DESCRIPTION OF THE DRAWINGS

Further features and advantages of the invention will be more clearly understood from the detailed description of some preferred, but not exclusive embodiments of a device for the manual metering of a fluid, illustrated by way of a non-limiting example with the aid of the accompanying drawings in which.

DETAILED DESCRIPTION OF SOME PREFERRED EMBODIMENT

Figure 1:
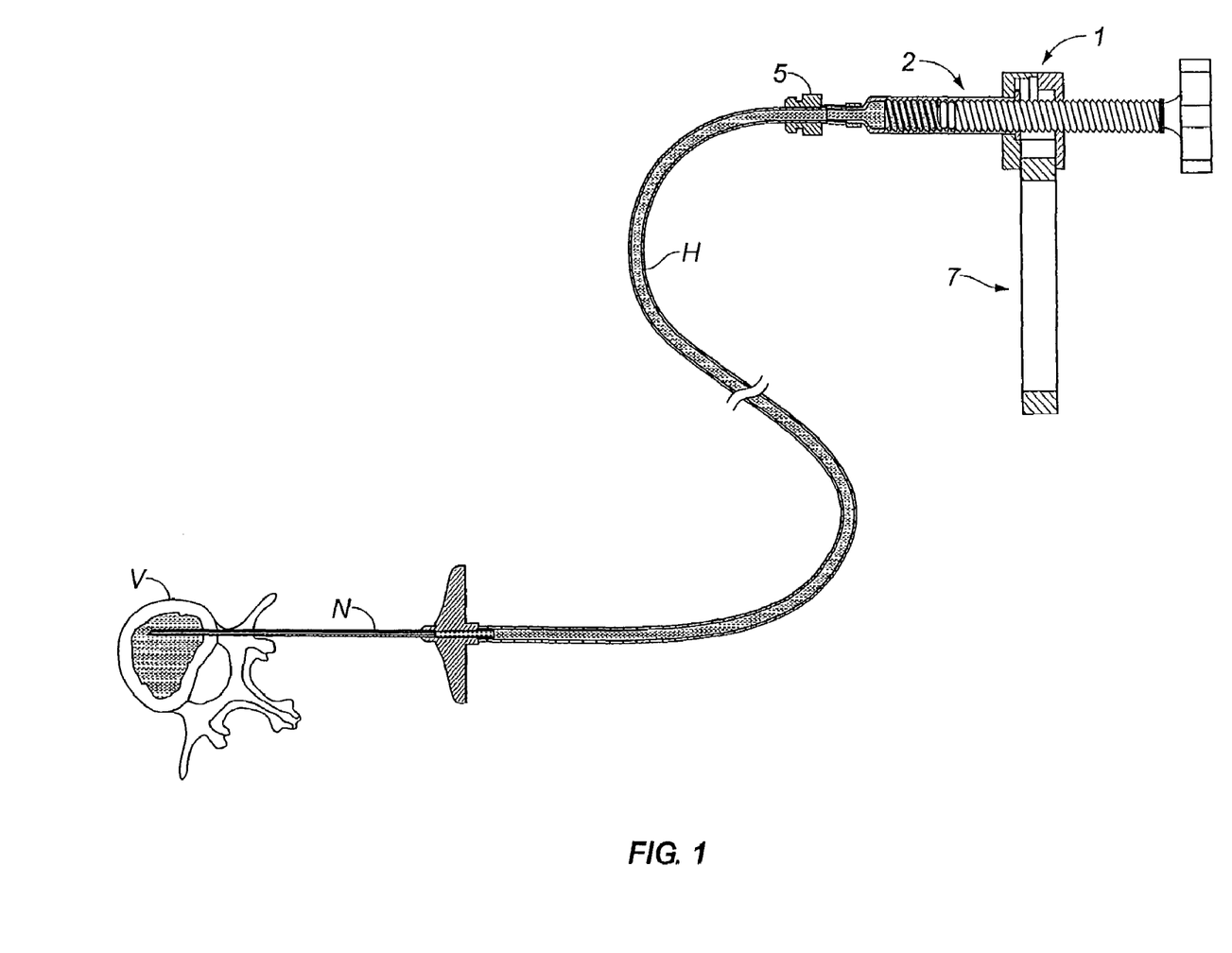
FIG. 1 shows a general view of the delivery device during use in a vertebral plastic surgery operation.
Figure 2:
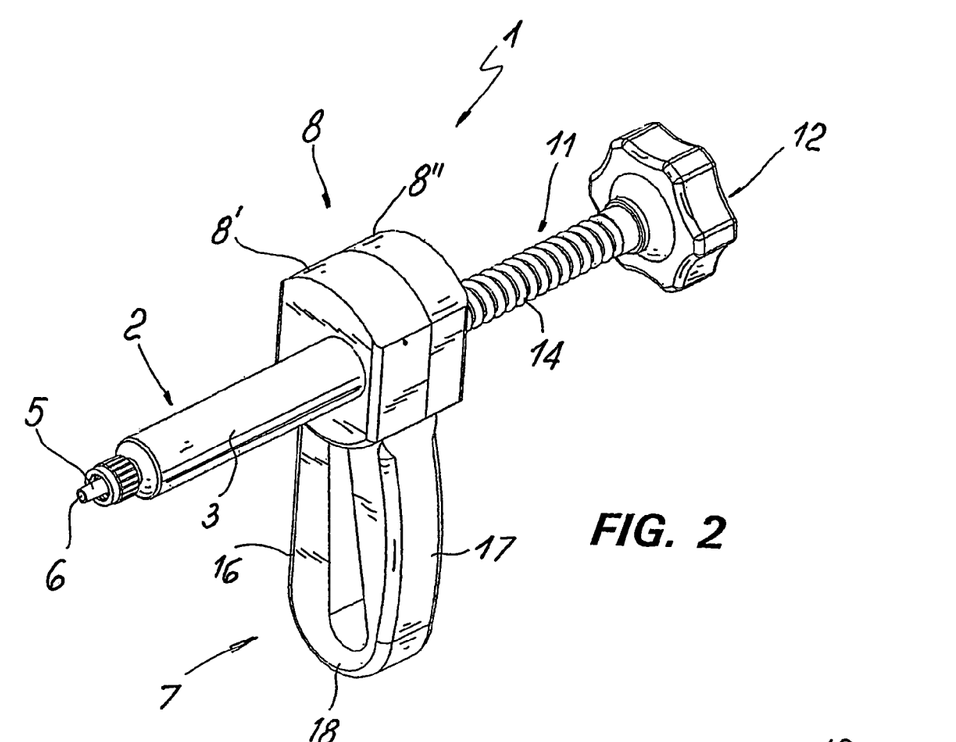
FIG. 2 shows a general perspective view of a first embodiment of the device shown in FIG. 1 in an assembled condition.
Figure 3:
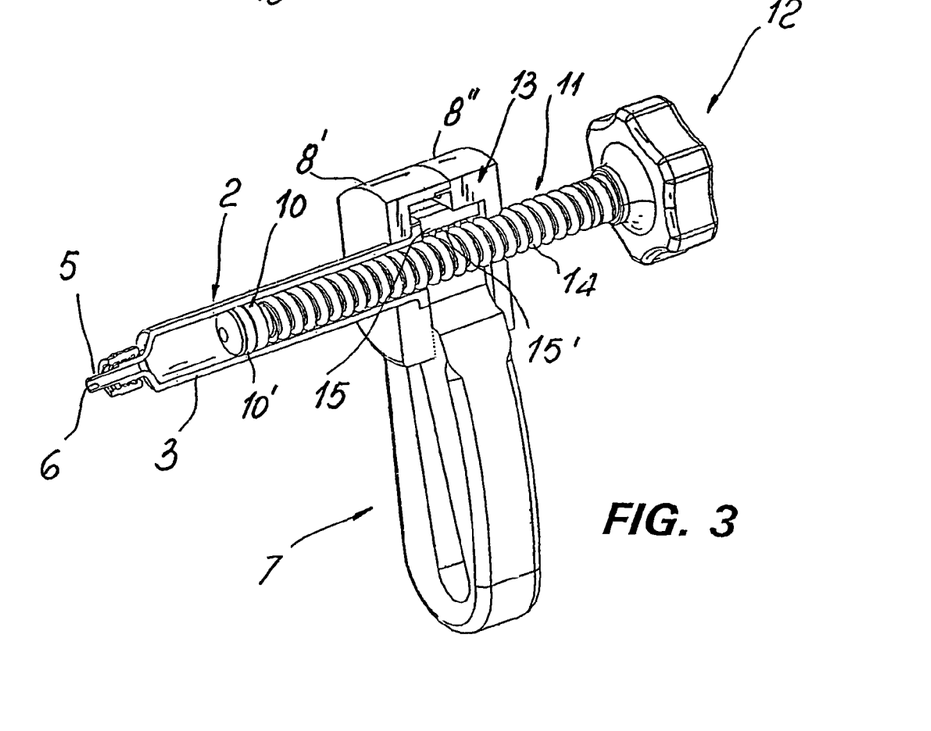
FIG. 3 shows a general perspective view of the device shown in FIG. 2 in partial cross-section and with some parts removed in order to make its components easier to see.
Figures 4, 5:
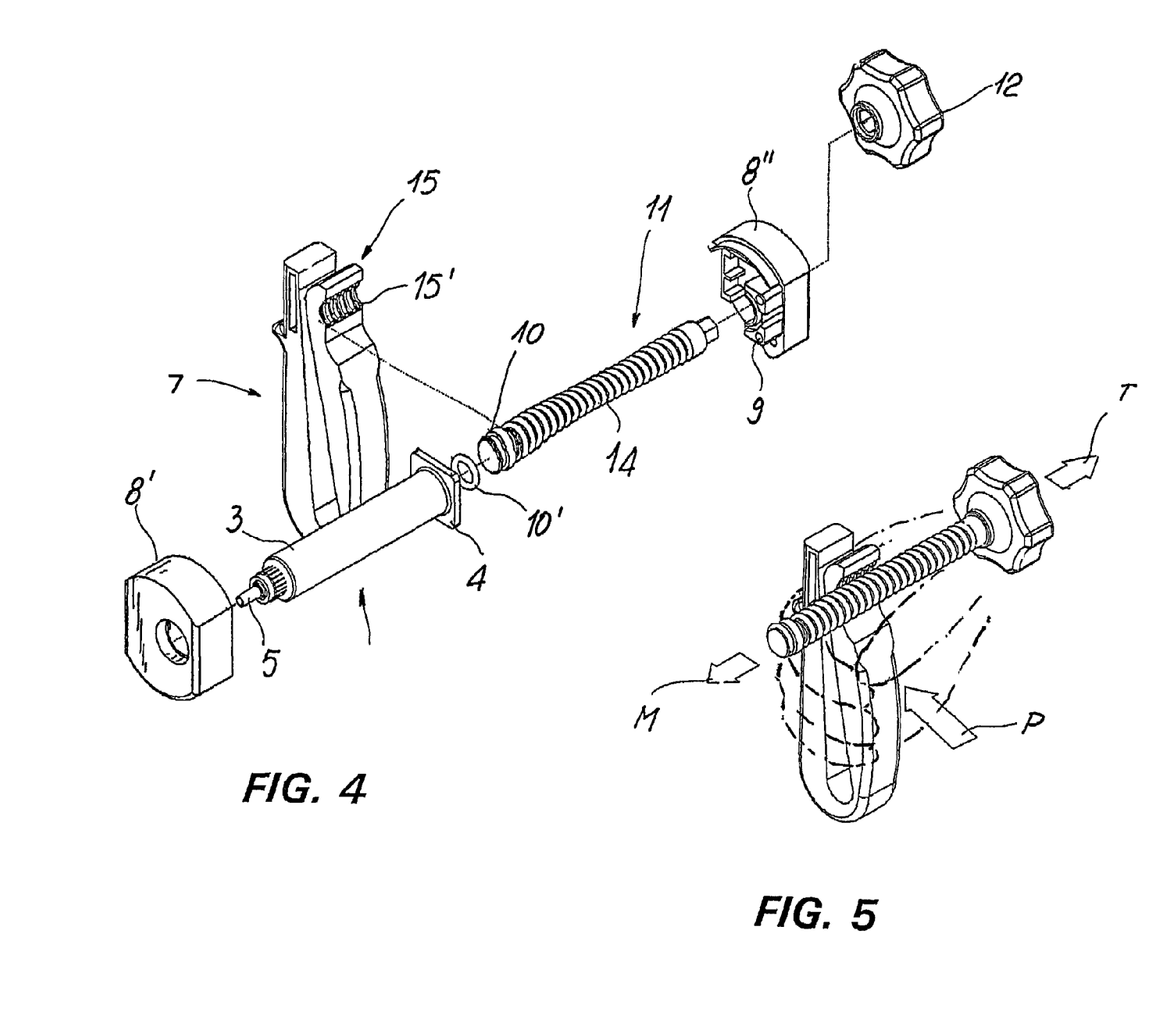
FIG. 4 shows an exploded perspective view of the device shown in FIG. 2.
FIG. 5 shows a perspective view of a sub-assembly of the device shown in FIG. 2 without some components so as to illustrate more clearly functioning of the device.
Figures 6, 7:
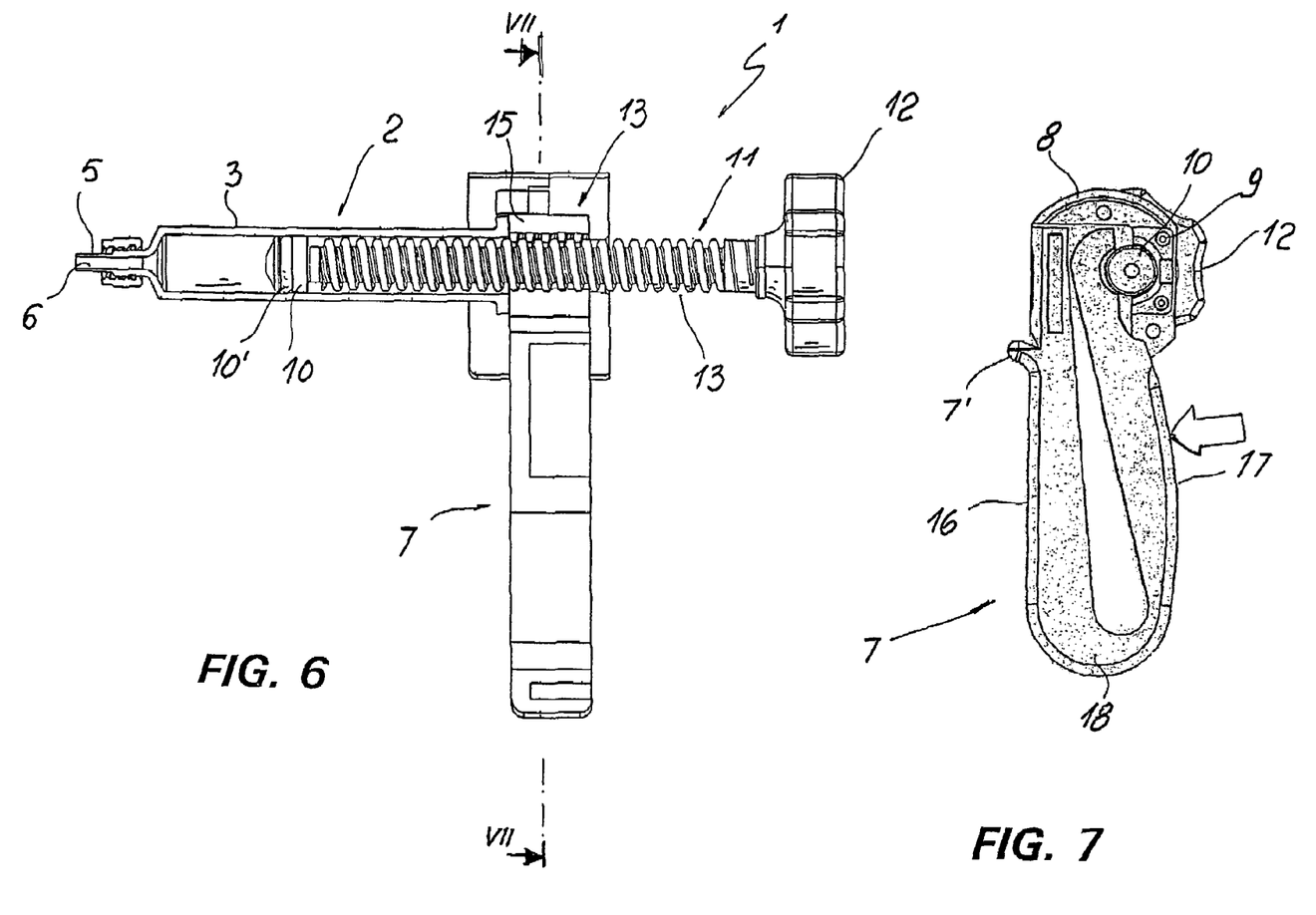
FIG. 6 shows a side view of the device shown in FIG. 2, partially cross-sectioned along a longitudinal axial plane.
FIG. 7 shows a front view of the device shown in FIG. 2, partially cross-sectioned along a plane indicated by the line VI-VI shown in FIG. 5.

With reference to FIG. 1, a metering device according to the invention is shown, said device being denoted in its entirety by reference number 1 and used to deliver a fluid, for example an acrylic resin or bone cement, manually into a location which is difficult to access, for example the inner cavity of a vertebra, by means of a thin tube H coupled to a needle N.

The device described hereinafter is particularly suitable for performing an orthopaedic surgery operation known as vertebral plastic surgery, for treating or restoring the continuity of a vertebra V affected by injuries or disease. It is clear, however, that the device may be used for other treatments and surgical or medical operations, using fluids of varying density or viscosity, or in other technological sectors, without thereby departing from the scope of the invention.

FIGS. 2-7 show a first embodiment of the device 1 which comprises a metering chamber 2 which has a substantially cylindrical side wall 3 and is intended to receive the hardening resin or bone cement inside it.

A longitudinal end of the side wall 3 of the chamber is open and stiffened by a radial flange 4. At the other end there is a tapered or funnel-shaped duct 5 with an opening 6 for the passage of the resin. A needle N may be connected to the funnel-shaped duct 5 directly or by means of the thin tube H so as to carry the resin to the site to be treated.

Optionally, the metering chamber 2 may be formed by the body of a traditional syringe made of plastic material, of the type which is widely available on the market, so as to reduce the cost of the device as a whole.

A handle, denoted in its entirety by reference number 7, may be associated with the chamber 2 by means of a suitable interface element 8. This element may be formed by two opposite shells 8', 8" which are coupled together by means of suitable connecting members 9 of the interlocking type or using any other adhesive means.

Advantageously, the walls of the shells 8', 8" may be provided with projections able to retain the handle 7 stably in the region of a bayonet-type lateral expansion 7' associated therewith as well as the radial stiffening flange 4 of the wall 3 of the metering chamber 2.

A piston 10 is housed inside the metering chamber 2, said piston optionally being provided with a sealing ring 10' and located at a longitudinal end of a rod 11 having keyed onto its opposite end a knob or other operating member 12, which may be grasped by a user in order to facilitate the expulsion of the resin located inside the chamber 2.

Conveniently, in order to actuate the rod 11 and expel the fluid or resin located inside it at high pressure and in a controlled manner, screw means are envisaged, said screw means being denoted in their entirety by reference number 13 and comprising a helical thread 14 formed on the cylindrical surface of the rod 11 and a female-thread element 15 which is able to engage with the thread 14 but is locked axially and rotatably with respect to the wall 3 of the chamber 2.

In this way, in order to perform micrometric feeding of the piston 10, with corresponding metering of the cement or fluid to be delivered, it is sufficient to grasp the knob 12 and make it rotate in a clockwise or anti-clockwise direction, depending on the direction of the thread 14, thereby causing the rod 11 to move axially and therefore the piston 10 to move inside the chamber 2 in the direction indicated by the arrow M.

In order to allow the piston 10 to slide freely inside the chamber 2 without using the screw means 13 and therefore speeding up the operations of filling the chamber 2, the screw means 13 may be modified so as to change from an active configuration to an inactive position and vice versa. In particular, the female-thread element 15 is formed by an internally threaded cylinder portion 15' which may be moved from an operative configuration—engaged with the thread 14 of the threaded rod 11 in order to allow micrometric feeding of the piston 10—to an inoperative configuration out of contact with the rod 11.

In this way, in order to draw the resin into the chamber 2, it is sufficient to disengage the female-thread element 15 from the thread 14 and pull the threaded rod in the direction of the arrow T by operating the knob 12.

Moreover, in the event of excessive pressure of the resin injected into the operating site, it is possible to reduce the pressure immediately by disengaging the female-thread element 15 from the thread 14 and therefore allowing the piston 10 to move backwards in the chamber 2.

According to the invention, the female-thread element 15 is formed integrally on the handle 7 in an area facing the threaded rod 11. Moreover, the handle 7 may be deformed elastically by means of simple transverse compression in the direction of the arrow P so as to move the female-thread element 15 into its inoperative configuration, i.e. separated from the thread 14, in order to prevent them from being engaged.

Preferably, the handle 7 is a substantially U-shaped unitary body with a first longitudinal end portion 16 which may be coupled to the chamber by means of the interface element 8 and a second longitudinal end portion 17 bearing the female-thread element 15.

Conveniently, the two longitudinal end portions 16, 17 of said U-shaped body are substantially rigid and are joined by an elastically deformable transverse intermediate portion 18.

In particular, the internally threaded cylindrical cylinder portion of the female-thread element 15 may be formed on the outer side of the longitudinal arm 17 of said substantially U-shaped body.

Even more in particular, the longitudinal arms 16, 17 are formed in such a way that the internally threaded cylindrical portion 15 is normally in contact with the thread 14 of the rod 11 and may be moved away from said rod by bringing the longitudinal arms 16, 17 of the knob 7 closer together transversally.

Conveniently, the corners of the longitudinal arms 16, 17 and of the transverse arm 18 are rounded so as to allow a user to grasp the handle and compress it easily with all the fingers of one hand, be it the left hand or the right hand, with ease even in the presence of body fluids and moisture in the surrounding environment.

The longitudinal arm 16 may have a bayonet-shaped free end which may be retained by first half-shell formations 8', 8" of the interface element 8.

In order to manufacture a device according to the invention, it is sufficient to make its various parts out of low-cost plastic material, then assemble it and sterilise it before it is packed.

In particular, all the components of the device may be made by means of the injection and moulding of low-cost plastic materials, providing that they allow the same end results to be obtained.

Owing to the significant constructional simplicity and low manufacturing cost, it is possible to use the device once only, avoiding the considerable costs of cleaning and sterilising the device.

It can be observed that the particular form and structure of the handle 7 allows the device to be gripped easily and stably and operated in a simple manner by any user, without any risk of malfunctions or slipping, even in the critical conditions that arise during a surgical operation.

Moreover, whenever it is necessary to reduce the feeding pressure of the resin delivered by the device, in the event of excessive pressure in the medullar cavity of the vertebra or the bone to be treated, it is sufficient to grip the handle 7 more tightly with all the fingers of the hand so as to disengage the female-thread element from the threaded rod 11 immediately, allowing the cement to flow back towards the metering chamber 2.

Figure 8:
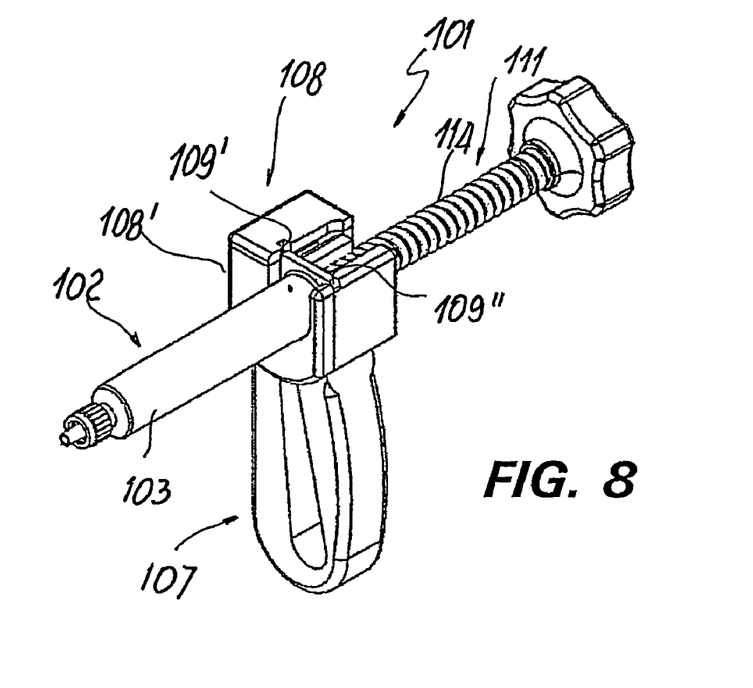
FIG. 8 shows a general perspective view of a second embodiment of the device shown in FIG. 1, in an assembled condition.
Figure 9:
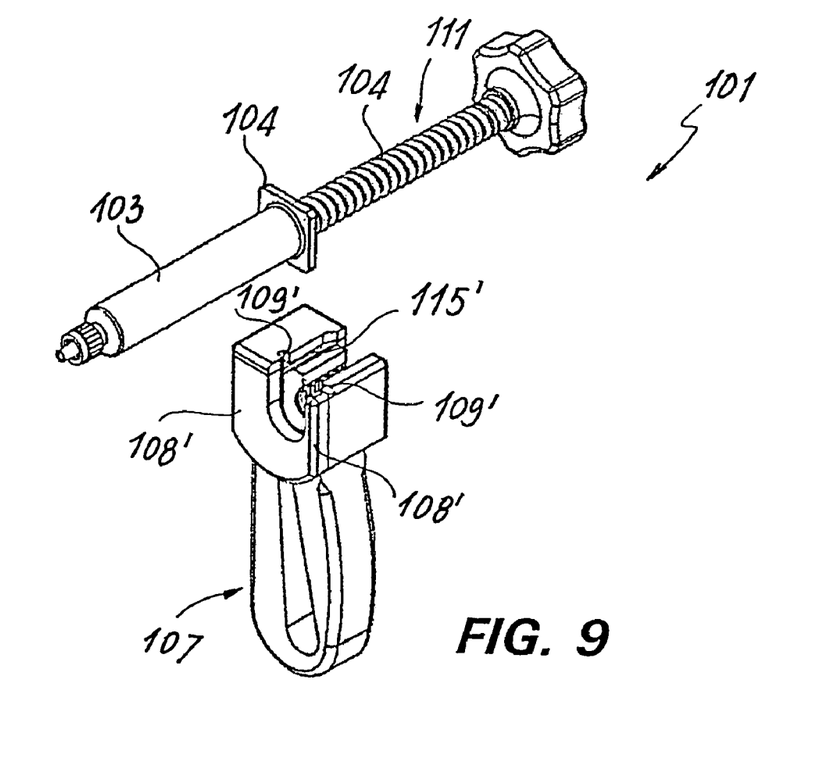
FIG. 9 shows a perspective view of the device shown in FIG. 8, with some parts separated from the rest of the device.

In the second embodiment shown in FIGS. 8, 9, denoted in its entirety by reference number 101, the same components that are also present in the first embodiment are identified by the same reference numbers increased by 100.

This second embodiment differs from the preceding embodiment only in respect of the interface element 108, which has the function of connecting the handle 107 to the metering chamber 102 formed by the body 103 of a traditional syringe with a stiffening flange 104.

The interface element 108 is essentially formed by a unitary block in the form of a U-piece with a pair of vertical arms 108', 108" which are provided internally with respective lateral slits 109', 109" able to receive and retain stably the lateral edges of the flange 104 of the body 103.

Therefore, in order to associate the metering chamber 102 with the handle 107, it is sufficient to couple the handle 107 to the interface element, insert the rod 111 inside the wall 103 of the metering chamber 102 and couple this chamber to the interface element 108 by inserting the flange 104 into the slits 109', 109" of the block 108.

In this way, it is even quicker and easier to prepare the device, and, if necessary, syringes 103' already filled with fluids to be metered and protected in sterile packaging may be used.

Operation of the handle for engaging and disengaging the partial female-thread 115 with/from the thread 114 is otherwise identical to that described for the device 1.

From the above, it is clear that the metering device achieves all the predefined objects and particular attention is drawn to the ease of handling in all operating is conditions, even the most difficult conditions, such as those which occur in moisture-affected environments, by all users, irrespective of which hand they normally use.

The metering device according to the invention may be subject to numerous modifications and variations, all of which fall within the inventive idea expressed in the claims. All the details may be replaced by other technically equivalent elements and different materials may be used according to the requirements, without departing from the scope of the invention.

Although the subject of the invention has been described with particular reference to the accompanying drawings, the reference numbers used in the description and in the claims are used to facilitate understanding of the invention and do not constitute any limitation on the protective scope claimed.

The instant application is based upon and claims priority of patent application no. VI2002A000140, filed on Jun. 26, 2002 in Italy, the disclosure of which is hereby expressly incorporated here in reference thereto.

The invention claimed is:

1. A device for the manual metering of a medical fluid comprising:
   a chamber for the fluid to be metered with an end opening,
   a gripping handle,
   a piston housed in said chamber and having an operating member for a user, and
   screw-type actuating means arranged in between said operating member and said piston so as to perform the longitudinal movement thereof and pressurize the fluid to be metered, said actuating means being changeable from a first configuration, where the piston is operable to be fed micrometrically, to a second configuration, where the piston is freely moveable in the chamber,
   said actuating means comprising an outer thread formed on the piston having a selected pitch, and a female-thread element formed integrally on said handle comprising a hollow cylindrical portion with an internal thread having a pitch corresponding to that of said outter thread and for engaging the thread on the piston,
   said handle comprising a substantially U-shaped unitary body with a first longitudinal end portion having a distal free end and a second longitudinal end portion adapted to be coupled to said chamber, and a second longitudinal end portion having distal free end carrying said female thread element and a proximal end, said first and second longitudinal end portions proximal ends being integrally connected end to end by a resilient member, said member being elastically deformable by means of transverse compression so as to move the actuating means between the first configuration and the second configuration, such that the outer thread and the female thread element engage when the handle is released and separated from one another when the handle is compressed.

2. A device according to claim 1, in which said longitudinal end portion of said handle are substantially rigid.

3. A device according to claim 1, in which said chamber is formed inside a substantially cylindrical wall, said end opening is tapered for connection to fluid transfer means, and a radial stiffening flange is formed at the open end.

4. A device according to claim 3, in which said chamber and piston comprises a syringe.

5. A device according to claim 3, comprising an interface element for coupling the handle to said metering chamber.

6. A device according to claim 5, in which said interface element comprises a pair of opposite box shaped half-shells having mutual coupling means, and first projections for engaging the first longitudinal end portion, and second projections for engaging for engaging the stiffening flange.

7. A device according to claim 5, in which said interface element has a substantially U-shaped form with substantially vertical arms having lateral slits for housing and fixing lateral edges of the stiffening flange.

8. A device according to claim 1, wherein the device is formed of plastic materials and is stored in sterile packaging for single use.

9. A device for the manual metering of a medical fluid comprising:
    a chamber for the fluid having an end opening,
    a gripping handle comprising a substantially U-shaped unitary body having a pair of rigid first and second spaced apart handle portions and an intermediate flexible connecting portion joining proximal ends of the first and second handle portions, said first handle portion having a free end and said second handle portion having a free end located between the free end of the first handle member and the chamber,
    a piston housed in said chamber having a threaded rod connected to the piston and having an outer thread and having an operating member for a user, and screw-type actuating means arranged between said operating member and said piston so as to perform the longitudinal movement thereof and pressurize the fluid to be metered, said actuating means being operable to change from an operative configuration, where the piston is fed micrometrically, to inoperative configuration, where the piston may move freely, where said actuating means comprises an outer thread associated with said piston and a female-thread element formed integrally on the free end of the said second handle portion, said female-thread element comprising a hollow cylindrical portion with an internal thread having a pitch corresponding to the thread on the rod, and said flexible connection portion being elastically deformable by means of transverse compression of the first and second handle portion so as o change spacing therebetween.

10. A device for manually metering medical fluid comprising:
    a cylinder having an interior chamber for receiving the fluid, said chamber having an outlet end with an outlet opening and an operating end having an opening;
    a piston engaging the interior chamber at the operating end of the cylinder and being reciprocally moveable longitudinally in the chamber between the operating end and the outlet end;
    a threaded rod having a distal free end and a proximate end secured to the piston, said rod being rotatable within the chamber and extending outwardly of the operating end of the cylinder;
    a turning handle secured to the distal free end of the rod for turning the rod;
    a holder engaging the operating end of the cylinder;
    a gripping handle for gripping the cylinder and the rod, comprising
    first and second handle members, each handle member having a first end located within the holder, and a second end located offset and remote from the cylinder, and an intermediate flexible connection joining the second ends of each handle member together; the first end of the first handle member engaging the holder to support the cylinder, and the first end of the second handle member located in the handle between the first end of the first handle member and the cylinder for lateral movement within the holder, said first end of the second handle member being formed with mating threads for engaging the threaded rod,
    said threaded portion of the second handle member being moveable away from the threads on the rod by a force driving the handle members towards each other to release the threads on the rod from the threaded portion of the second handle member to thereby allow the rod and piston to move between the operating end and the outlet end by a force exerted along the rod, said flexible connection between the first and second handle members being normally biased so that the mating threads engage the threaded rod, such that the piston is moveable between the outlet and operating end only by rotating the turning handle, and said gripping handle being transversely squeezable to overcome the bias of the flexible connection causing the first and second handle members to move towards each other such that the threaded portion of the second handle member disengages with the threaded rod so that the rod is moveable longitudinally in the cylinder by a force exerted there along in a direction extending between the outlet and the operating end thereof.

* * * * *